United States Patent
Sawada

(10) Patent No.: US 8,598,340 B2
(45) Date of Patent: Dec. 3, 2013

(54) SPIROOXAZINE RADICAL DERIVATIVES AND REVERSIBLE ISOMERIZATION REACTION

(71) Applicant: NEC Corporation, Tokyo (JP)

(72) Inventor: Atsumasa Sawada, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 13/667,701

(22) Filed: Nov. 2, 2012

(65) Prior Publication Data

US 2013/0072678 A1 Mar. 21, 2013

Related U.S. Application Data

(63) Continuation of application No. 12/809,203, filed as application No. PCT/JP2007/074542 on Dec. 20, 2007, now Pat. No. 8,329,896.

(51) Int. Cl.
*C07D 498/10* (2006.01)
*C07D 517/10* (2006.01)

(52) U.S. Cl.
USPC .............................................. 544/6; 548/215

(58) Field of Classification Search
USPC ............................................................ 544/6
See application file for complete search history.

(56) References Cited

FOREIGN PATENT DOCUMENTS

JP   H06138577 A   5/1994

OTHER PUBLICATIONS

Japanese Office Action for JP2007-241225 mailed on Nov. 20, 2012.
Campredon, M et al., Gazzetta Chimica Italiana, 1993, vol. 123, No. 5, p. 261-264.

*Primary Examiner* — Kahsay Habte

(57) ABSTRACT

The present invention can provide new spirooxazine radical derivatives of the following general formula (1) which have chromic property enabling the distinction between the radical species and the cation species on the basis of absorption wavelength:

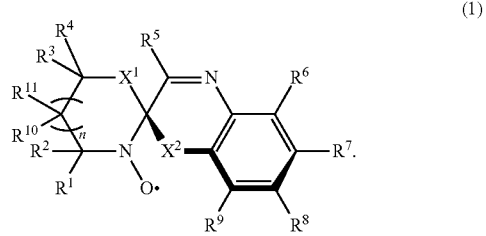

(1)

6 Claims, No Drawings

SPIROOXAZINE RADICAL DERIVATIVES AND REVERSIBLE ISOMERIZATION REACTION

TECHNICAL FIELD

The present invention relates to spirooxazine radical derivatives having chromic property that radical species are generated or destroyed, with reversible coloring and decoloring, by applying light or electric energy, and the reversible isomerization reaction of spirooxazine derivatives.

BACKGROUND ART

A radical compound is in highly activated state, so it has been customarily applied in various uses. For example, a radical initiator used as an initiator of polymerization in synthesis of polymer compound may be mentioned.

However, most radical compounds are unstable and destroy the radical state in the short period.

Among them, it is known that a nitroxy radical (>N—O.) is relatively stable and possible to maintain in radical state. For example, a compound having the nitroxy radical in molecule, 4-hydroxy-2,2,6,6-tetramethylpiperidine-1-oxyl (TEMPOL) is used as a spin labeling agent used for electron spin resonance analysis (ESR). In addition, this compound has been also studied for a medical application, and it is promised as a radiation protective agent used in cancer radiation therapy (e.g. see S. M. Halm, etc., "Evaluation of TEMPOL radioprotection in murine tumor model", Free Rad. Biol. Med., 22, 1211-1216 (1997)).

Further, there is an organic radical polymer used in a non-aqueous electrolyte secondary cell, which was developed during developing remarkably in electronics in recent years and which would be expected in rapid charge/discharge (e.g. see JP2005-209498A).

The organic radical polymer performs as an active material of secondary cell and can achieve electrochemically a reversible oxidation-reduction reaction. In this oxidation-reduction reaction, when a nitrosonium (cation) is regulated by reversible electron exchange from outside between nitroxy radical and nitrosonium, the electron is emitted as counter anion and thus an electric current is induced.

A chromic compound has two different chemical species in a single compound and each of them has different light absorption wavelengths. So, it has a function to induce a reversibly structural isomerization between each species by external factors such as light, electricity and heat.

As a chromic compound, many compounds such as spiropyran and spirooxazine compounds are known (e.g. see the Chemical Society of Japan, Kikan Kagaku Sosetsu, No. 28 "Chemistry of Organic Photochromism", P70-88 (1996)). It is known also that these compounds are an organic compound which is synthesized in high latitude and that derivatives obtained from each group of these compounds can give different feature to the individual compound.

For example, since the spiropyran compound has a carbon-carbon double bond portion (—C=C—) acting as a chromophore in the pyran ring and the bond portion has a structure which is easily auto-oxidized by singlet oxygen, it is to say that the term maintaining durability of reversible isomerization of the compound is short.

The spirooxazine compound has a structure that the pyran ring of spiropyran compound is replaced with an oxazine ring and a carbon-nitrogen double bond portion (—C=N—), which is the chromophore on the oxazine ring, is attacked by singlet oxygen as the pyran ring of the spiropyran compound. However, because it is considered that the attack of the carbon-nitrogen double bond by singlet oxygen is difficult compared with the carbon-carbon double bond, its degradation by automatic oxidation becomes hard, and thus its durability of reversible isomerization is improved. Therefore, in the spiro compound which exhibits chromic property with high repeating durability, spirooxazine compound is preferable, and for example, it is applied as a functional pigment.

In addition, the conventional spirooxazine compound directly introduced a group having radical, an instable chemical species, is not known, although the conventional spirooxazine compound introduced a stable substituent such as hydroxyl, alkyl, aryl, aralkyl, alkoxyalkyl, alkylcarbonyl, and alkoxycarbonylalkyl groups onto the nitrogen in the heterocyclic ring forming one side of the sprio ring such as indoline, thioline, and selenazoline rings are known (e.g. see the Chemical Society of Japan, Kikan Kagaku Sosetsu, No. 28 "Chemistry of Organic Photochromism", P70-88 (1996), JP 2000-026469A).

As a stable radical compound, some heterocyclic ring compounds having nitroxy radical group are present, and in addition to the above TEMPOL, spin adduct of 5,5-dimethyl-1-pyrroline-N-oxide, 3-carbamoyl-2,2,5,5-tetramethylpyrrolidine-1-oxyl, 4-carbamoyl-2,2,6,6-tetramethylpiperidine-1-oxyl, 4-metacryloyloxy-2,2,6,6-tetramethylpiperidine-1-oxyl are known.

These heterocyclic ring compounds having stable nitroxy radical group change reversibly between nitroxy radical and nitrosonium ion when giving different potentials. In other words, they show reversible oxidation-reduction reaction and exchange of electrons occurs. However, for the reversible state change of oxidation-reduction reaction of organic radical compounds having a stable radical group such as nitroxy radical, there was no method to measure it other than direct measurement of the oxidation-reduction potential.

Consequently, an problem of the present invention is to provide new spirooxazine radical derivatives which exhibit chromic property, which has both stable radical group contributing to generation of oxidation-reduction reaction and chromophore contributing to the chromic property to control oxidation-reduction reaction of organic radical compounds by giving different wavelength light, can removes color change also in case that there is a change in absorption spectrum accompanied with photoisomerization and there is an absorption in visible range, and can identify the generated state of radical and cation species by difference of absorption wavelengths.

DISCLOSURE OF INVENTION

In order to solve the above problem, the inventor found that the problem was solved by that a stable radical species, nitroxy radical region (>N—O.) is formed in the ring such as pyrrolidine, pipperidine, oxazolydine, oxazine, thiazoline, tiazine, selenazoline, or selenazine ring which forms spiroring to the oxazine ring of the spirooxazine compound which exhibits the chromic property, in other words, by introducing an oxygen radical on the nitrogen adjacent to the spiro-carbon, and eventually achieved the present invention.

The present invention relates to spirooxazine radical derivatives of the following general formula (1):

[Formula 1]

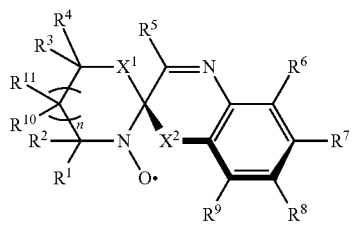

wherein, $X^1$ is a chalcogen element, alkylidene or cycloalkylidene group, $X^2$ is a chalcogen element, $R^1$ to $R^{11}$ are, independently each other, hydrogen atom, alkyl with 1 to 4 carbons, alkoxy, aryl, halogenated alkyl, cyano, amino, or nitro group, or halogen atom, or any of $R^1$ to $R^{11}$ bonded to carbon atoms adjacent to each other may form in combination an aromatic or heterocyclic ring which has optionally a substituent; and n is 0 or 1.

The present invention also relates to reversible isomerization between a spiro type structure in the general formula (1) and a ring-opened body represented by the general formula (2) of spirooxazine radical derivatives, as shown in the following reaction scheme I:

Reaction Scheme I

[Formula 2]

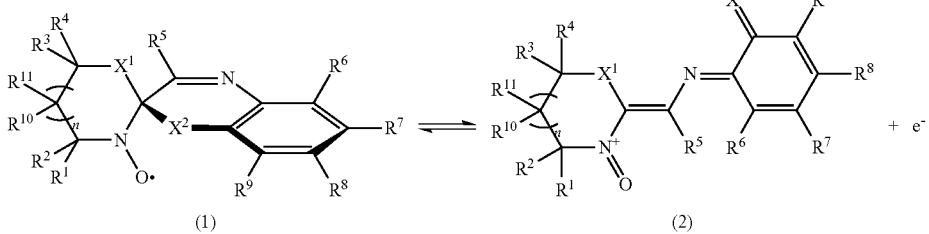

wherein, $X^1$, $X^2$, $R^1$ to $R^{11}$ and n are the same as mentioned above.

BEST MODE FOR CARRYING OUT THE INVENTION

The present invention relates to spirooxazine radial derivatives represented by the above general formula (1), in which a 5-member or 6-member heterocyclic ring and an oxazine derived heterocyclic ring form a spiro structure and an oxygen radical binds to the nitrogen of the 5-member or 6-member heterocyclic ring adjacent to the sprio-carbon.

$X^1$ in the general formula (1) is a chalcogen element, alkylidene or cycloalkylidene group. Additionally, the chalcogen element may be mentioned oxygen, sulfur, selenium atom, etc. Here, two alkyl groups of the alkylidene group may be same or different each other.

When $X^1$ is a chalcogen element, it contributes to stabilization of the nitroxy radical, oxygen atom is the most preferable, and sulfur atom and selenium atom are preferable in this order. When $X^1$ is alkylidene group, it is preferable that the two alkyl groups composing of an alkylidene group have, individually each other, 1 to 5 of carbons, and 1 to 3 of carbons are preferable for stabilization of the nitroxy radical. Specifically, methyl, ethyl, propyl, and isopropyl groups are mentioned. Similarly, when $X^1$ is a cycloalkylidine group, the 5 to 7 of carbons are preferable.

$X^2$ is a chalcogen element, such as oxygen, sulfur, or selenium atom, and the oxygen atom with smaller atomic weight is preferable because of stabilization of the nitroxy radical. When $X^2$ is oxygen atom, the above 6-member ring is an oxazine ring. However, in this specification, even if $X^2$ is a chalcogen element other than oxygen atom, the ring is also referred as an oxazine ring for convenience.

$R^1$ to $R^{11}$ are, independently each other, hydrogen atom, alkyl, alkoxy, aryl, halogenated alkyl, cyano, amino, nitro, or halogen group. Additionally, $R^1$ to $R^{11}$ located in the adjacent carbons may form, with these carbon atoms, an aromatic or heterocyclic ring which may have a substituent. When $R^1$ to $R^{11}$ are alkyl groups, 1 to 4 of carbons are preferable. In particular, $R^1$, $R^2$ and $R^5$ are preferably methyl groups for stabilization of the nitroxy radical.

In addition, when $R^1$ to $R^{11}$ located in the adjacent carbon atom are combined together, they may form an aromatic ring, such as benzene, naphthalene, anthracene, or phenanthrene ring, or a heterocyclic ring such as pyridine, pyrimidine, isoquinoline, quinazoline, acridine, or benzoacridine ring, with these carbon atoms. Moreover, the aromatic or heterocyclic ring may be substituted with an electron-donative group such as alkyl, alkoxy, or amino group or an electron-attractive group such as nitro, cyano, halogenated alkyl, alkyl-carbonyl, alkyl-ester, or halogen group.

Accordingly, it means that when n is 0, $R^1$, $R^2$, $R^3$ and $R^4$ located in the adjacent carbons may form an aromatic ring or a heterocyclic ring with the carbon atoms and that when n is 1, an aromatic ring or a heterocyclic ring may be formed with combination of $R^1$, $R^2$, $R^{10}$ and $R^{11}$ or $R^{10}$, $R^{11}$, $R^3$ and $R^4$ located in the adjacent carbons. In case that the ring formation is a heterocyclic ring, when the carbons have double bond or are conjugated or the ring is a hetero-aromatic ring, all of the 4 groups participate in ring formation. However, when the ring formed from the carbon atoms has saturated bonds on both sides or has an unsaturated bond on either side, 1 or 2 groups among the 4 groups do not participate in ring formation in forming a heterocyclic ring. Accordingly, these are also included in the above.

It means that $R^6$ to $R^9$ on a benzene ring bound with the oxazine ring, in lying next to each other, may further form an aromatic ring such as benzene, naphthalene, anthracene, or phenanthrene ring, or a heterocyclic ring such as pyridine, pyrimidine, isoquinoline, quinazoline, acridine, or benzoacridine ring to the benzene ring.

In the above, for stabilization of the nitroxy radical, the structure without an aromatic or heterocyclic ring is preferable. But, if an aromatic ring is introduced, the smallest benzene ring is the most preferable, and naphthalene, anthracene, and phenanthrene rings are preferable in this order. Similarly, if a heterocyclic ring is introduced, the smallest pyridine ring is the most preferable, and pyrimidine, isoquinoline, quinazoline, acridine, and benzoacridine rings are preferable in this order.

These aromatic or heterocyclic rings may be substituted with an electron donative group such as alkyl, alkoxy, or amino group or an electron attractive group such as nitro, cyano, halogenated alkyl, alkyl-carbonyl, alkyl-ester, or halogen group. Because the electron donative and attractive groups have a function as auxochrome group, the light absorption wavelength can be moved toward longer wavelength by introducing an electron donative group and toward shorter wavelength by introducing an electron attractive group.

In the general formula (1), n is 0 or 1.

The structures of the precursors of spirooxazine radical derivatives of the present invention can be identified by proton nuclear magnetic resonance analysis ($^1$H-NMR), carbon nuclear magnetic resonance analysis ($^{13}$C-NMR), infrared spectrometric analysis (FT-IR), elementary analysis and the like. The spirooxazine radical derivatives of the present invention themselves can be identified by electron spin resonance (ESR).

The spirooxazine radical derivatives of the present invention are not limited particularly for their synthesis method, and the following method may be illustrated as a simple synthesis process with relatively few steps.

Reaction between a compound A of the following general formula (3) and a compound B of the following general formula (4) is proceeded in the presence of a solvent such as methanol, ethanol, toluene, tetrahydrofuran, or N,N-dimethylformamide with reflux under an inactive atmosphere such as nitrogen and argon.

[Formula 3]

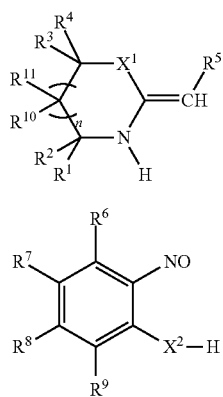

(3)

(4)

In the formulae (3) and (4), $X^1$, $X^2$, $R^1$ to $R^{11}$ and n are the same as described above.

Although the reaction ratio between the compound A and the compound B is depended on the intended yield, it is preferably in the range of 1 mol/3 mol to 3 mol/1 mol. The reaction product obtained here becomes the compound C of the following general formula (5).

[Formula 4]

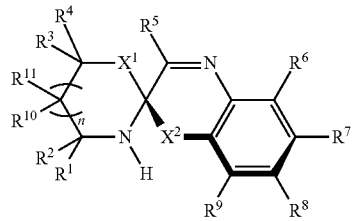

(5)

In the formula (5), $X^1$, $X^2$, $R^1$ to $R^{11}$ and n are the same as described above.

Then, hydrogen peroxide is added dropwise into the compound C with avoiding abnormal overheating to oxidize the second amine part in hydroxyaminization, and the compound D of the following general formula (6) (an intermediate product), a precursor of spirooxazine radical derivatives, is obtained.

[Formula 5]

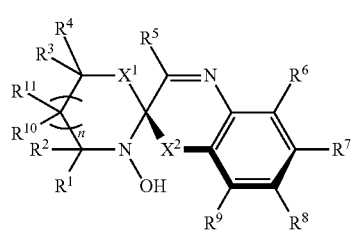

(6)

In the formula (6), $X^1$, $X^2$, $R^1$ to $R^{11}$ and n are the same as described above.

Finally, the compound D is resolved in a sufficiently dehydrated organic solvent, such as ether, chloroform, ethyl acetate, hexane, or acetonitrile, and after adding silver oxide with cooling by ice, the resultant solution is stirred sufficiently. By-product water is dehydrated and removed by adding anhydrous sodium sulfate. After removed residual solid by filtering, the filtrate is concentrated in vacuum with a rotary evaporator or the like. In this concentration process, without removing the solvent thoroughly, the solvent is remained 2 or 3 more times than the residual material. The residue is cooled at low temperature by the mixture of ethanol and dry ice and the like, the spirooxazine radical derivatives E of the present invention are obtained.

The spirooxazine radical derivatives of the present invention induce the reversible change of the light absorption spectrum by resolving them in organic solvents such as methylene chloride, chloroform, hexane, toluene, N,N-dimethylformamide, and tetrahydrofuran, and by the light of visible light area in 400 nm to 750 nm or ultraviolet range in 250 nm to 400 nm in order to induce a reversible change as shown in the below reaction scheme I. Confirming this change of state can be achieved by observing the reversible state change in the change of absorbance of two different absorption peaks by use of ultraviolet-visible spectrophotometer, and particularly, in case of presence of absorption in visible range, the change between colored and decolored states can be observed as a reversible color change. The reversible generation and destruction of radical in change between two states can be observed by electron spin resonance (ESR) analysis. In addition, by performing cyclic voltammetry (CV) measurement for the spirooxazine radical derivatives, their potential changes depending on the reversible oxidation-reduction reaction can be observed.

Reaction scheme I

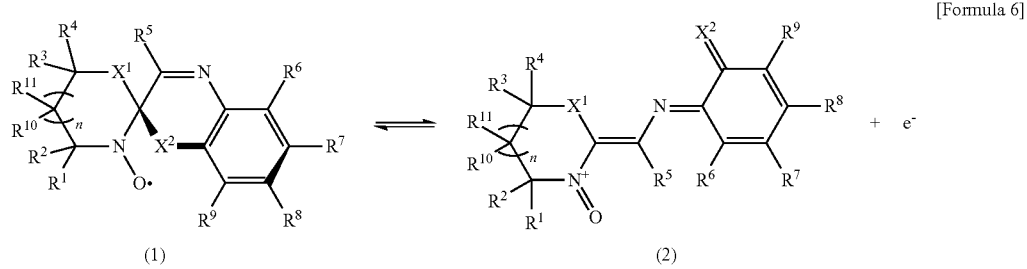

In the above reaction scheme I, $X^1$, $X^2$, $R^1$ to $R^{11}$ and n are the same as described above.

In the reaction scheme I, the structure of cation species which an electron has completely separated is shown. However, depending on the combination of $X^1$, $X^2$, $R^1$ to $R^{11}$ and n, in the intermediate state, the structure pairing a cation species and an electron or a radical shaped structure in the state before separating an electron in the ring-open state in the general formula (2) may be present.

The spirooxazine radical derivatives of the present invention can be used for various applications such as secondary cell, by using oxidation-reaction reaction as shown in the reaction scheme I.

EXAMPLES

Examples of the present invention are illustrated as follows. But they do not restrict the invention.

Example 1

2-Methylene-3,3,5,5-tetramethylpyrrolidine (3 mmol (417 mg)) shown in the following formula (7) as compound A and 2-nitrosophenol (3 mmol (369 mg)) as compound B were solved in 40 ml of dehydrated methanol, heated and refluxed for 3 hours, and then the solvent was distilled off. The obtained residual reactant was developed and separated with silica gel column (development solvent: ethyl acetate/normal hexane solvent mixture), and the solution of the compound (C-1) of the following formula (8) was obtained. By removing solvent sufficiently from the obtained solution through vacuum distillation, the purified compound (C-1) was obtained.

[Formula 7]

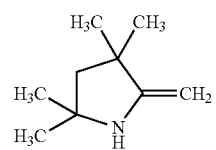

(7)

[Formula 8]

(8)

Then, by dropping excess amount of hydrogen peroxide to 0.61 mmol (150 mg) of the compound (C-1) in dehydrated ether to avoid abnormal heating, the compound (D-1) of the following formula (9) was obtained.

[Formula 9]

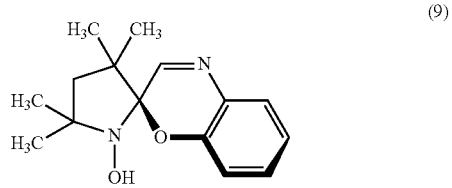

(9)

The compound (D-1) (0.50 mmol (130 mg)) was put into 30 ml of dehydrated ether and stirred sufficiently after adding 0.50 mmol (116 mg) of silver (I) oxide. After adding anhydrous sodium sulphate, suction filtration was performed. The obtained filtrate was vacuum concentrated to ½ volume by rotary evaporator. By cooling the residual solution at low temperature (−78° C.) by the mixture of ethanol and dry ice, the spirooxazine radical derivative (E-1) of the following formula (10) was obtained.

[Formula 10]

(10)

The radical generation of the spirooxazine radical derivative (E-1) could be observed by electron spin resonance (ESR) analysis. Structures of the above reaction materials, intermediate products, and spirooxazine radical derivative were shown in the table $1^{st}$ (Table 1 to 3). In addition, the measurement results of $^1$H-NMR (solvent: CDCl$_3$, standard: TMS) and results of elemental analysis for intermediate products (C-1, D-1) were shown in the table $2^{nd}$ (Table 4, 5).

Examples 2 to 15

As performed like Example 1, various spirooxazine radical derivatives as shown in Table $1^{st}$ were prepared using starting materials shown in Table $1^{st}$. The structures of intermediate products in these Examples were shown in the Table $1^{st}$ (Table 1 to 3). In addition, the measurement results of ¹H-NMR (solvent: CDCl₃, standard: TMS) and results of elemental analysis for intermediate products were shown in the Table 2$^{nd}$ (Table 4, 5).

TABLE 1

Table 1$^{st}$-1

| | Starting Material | |
|---|---|---|
| Example | Compound A | Compound B |
| 1 | [structure: 3,3,5,5-tetramethyl-2-methylenepyrrolidine] | [structure: 2-nitrosophenol] |
| 2 | [structure: 3,3-dimethyl-2-ethylidene-indoline] | [structure: 4-nitro-2-nitrosophenol] |
| 3 | [structure: 3-methyl-3-propyl-2-(piperidinomethylene)indoline] | [structure: 4-nitro-2-nitrosophenol] |
| 4 | [structure: 3,3,5,5-tetramethyl-2-methylenepyrrolidine] | [structure: 3-nitroso-2-naphthol] |
| 5 | [structure: spiro cyclopentane-pyrrolidine with methylene] | [structure: 4-cyano-2-nitrosophenol] |

| | Intermediate Product | |
|---|---|---|
| Example | Compound C | Compound D |
| 1 | [structure: spiro pyrrolidine-benzoxazine, NH] | [structure: spiro pyrrolidine-benzoxazine, N-OH] |
| 2 | [structure: spiro indoline-nitrobenzoxazine, NH] | [structure: spiro indoline-nitrobenzoxazine, N-OH] |

TABLE 1-continued
| | | |
|---|---|---|
| 3 | 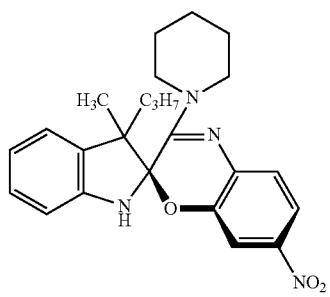 | 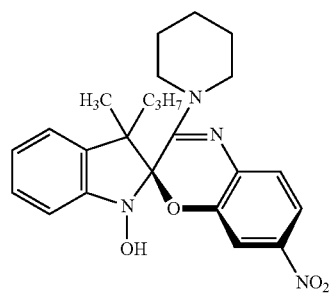 |
| 4 | 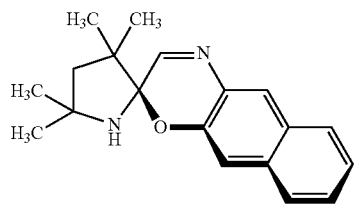 | 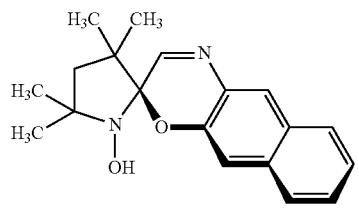 |
| 5 | 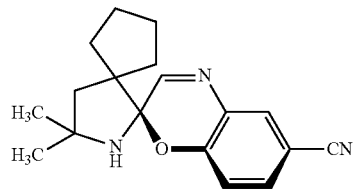 | 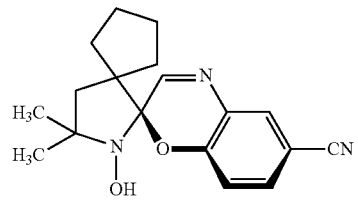 |
| Example | Derivative of this Invention Spirooxazine Radical Derivative E |
|---|---|
| 1 | 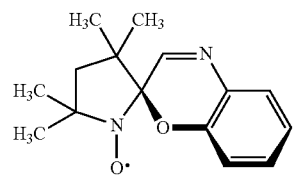 |
| 2 | 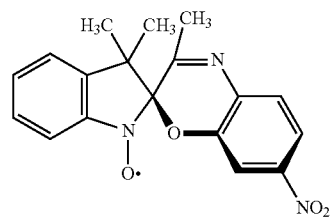 |
| 3 | 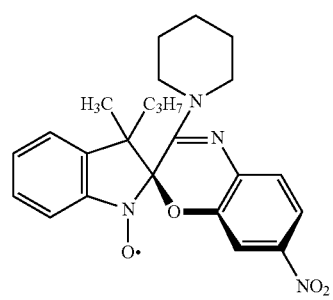 |

TABLE 1-continued
| 4 | 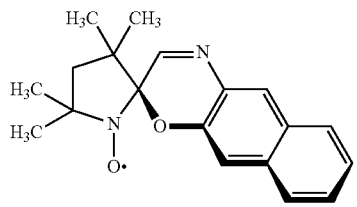 |
| --- | --- |
| 5 | 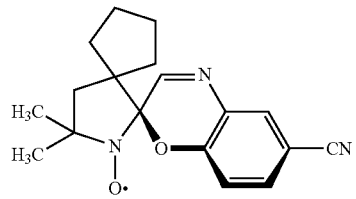 |
TABLE 2
Table 1st-2
| Example | Starting Material | |
| --- | --- | --- |
| | Compound A | Compound B |
| 6 | 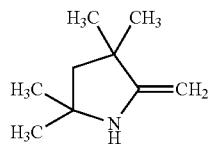 | 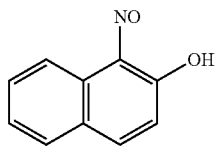 |
| 7 | 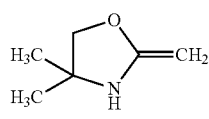 | 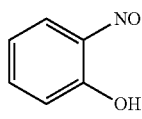 |
| 8 | 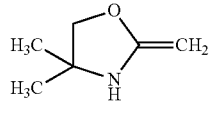 | 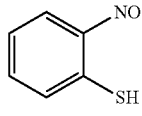 |
| 9 | 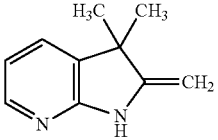 | 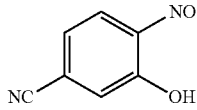 |
| 10 | 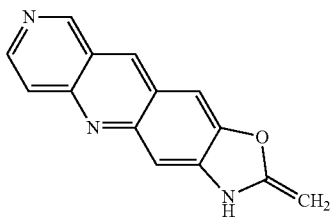 [SMILES: C=C1Nc2cc3nc4ccncc4cc3cc2O1] | 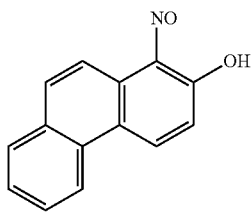 |

TABLE 2-continued

| | Intermediate Product | |
|---|---|---|
| Example | Compound C | Compound D |
| 6 | [structure] | [structure] |
| 7 | [structure] | [structure] |
| 8 | [structure] | [structure] |
| 9 | [structure] | [structure] |
| 10 | [structure] | [structure] |

| Example | Derivative of this invention Spirooxazine radical Derivative E |
|---|---|
| 6 | [structure] |
| 7 | [structure] |

TABLE 2-continued
| | | |
|---|---|---|
| | 8 | 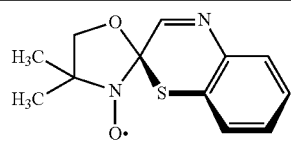 |
| | 9 | 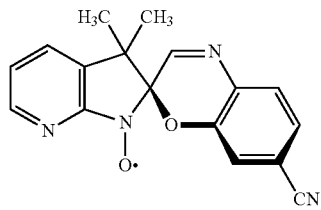 |
| | 10 | 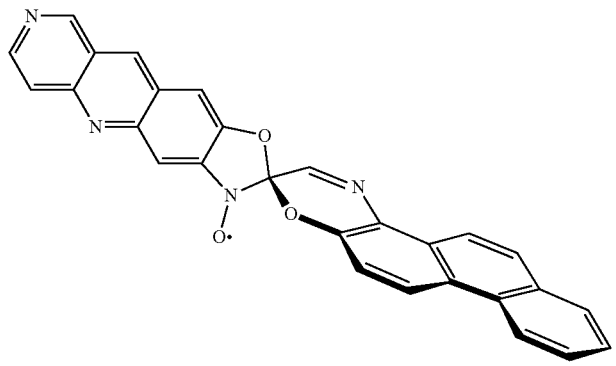 |
TABLE 3
Table 1st-3
| Example | Starting Material | |
|---|---|---|
| | Compound A | Compound B |
| 11 | H3C, CH3 ring with O, NH, =CH2 | nitrosophenol with OH |
| 12 | Se-containing ring with NH, CH3, CH3, =CH2 | O2N, NO, OH, NO2 substituted benzene |
| 13 | S-containing ring with C3H7, =CH, NH, CH3, CH3 | NC, NO, OH substituted benzene |

TABLE 3-continued

| Example | | |
|---|---|---|
| 14 | 3,3,5,5-tetramethyl-2-methylene-piperidine structure | 2-nitroso-3-methoxyphenol structure |
| 15 | 3,3-dimethyl-2-methylene-tetrahydro-1,8-naphthyridine structure | 2-nitrosophenol structure |

| | Intermediate Product | |
|---|---|---|
| Example | Compound C | Compound D |
| 11 | spiro oxazine with NH | spiro oxazine with N–OH |
| 12 | selenium-containing spiro oxazine with dinitro, NH | selenium-containing spiro oxazine with dinitro, N–OH |
| 13 | selenium-containing spiro oxazine with CN, C₃H₇, NH | selenium-containing spiro oxazine with CN, C₃H₇, N–OH |
| 14 | piperidine spiro oxazine with OCH₃, NH | piperidine spiro oxazine with OCH₃, N–OH |
| 15 | naphthyridine spiro oxazine with NH | naphthyridine spiro oxazine with N–OH |

| Example | Derivative of this invention Spirooxazine Radical Derivative E |
|---|---|
| 11 | spiro oxazine with N–O• radical |

TABLE 3-continued
| | |
|---|---|
| 12 | 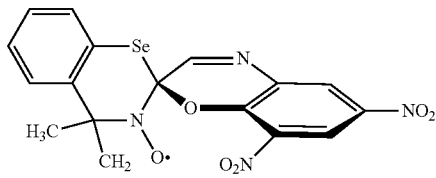 |
| 13 | 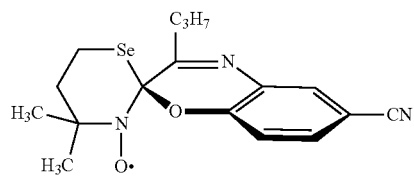 |
| 14 | 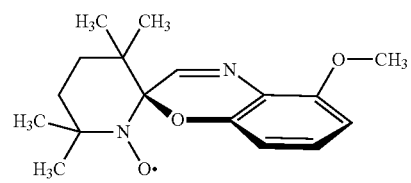 |
| 15 | 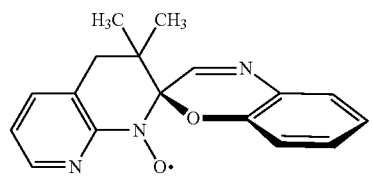 |
TABLE 4
Table 2$^{nd}$-1
| | Compound C | | | | | Compound D | | | |
|---|---|---|---|---|---|---|---|---|---|
| | Elemental Analysis | | $^1$H-NMR | | | Elemental Analysis | | $^1$H-NMR | |
| Example | El. | Calcd. | Anal. | ppm | H content | El. | Calcd. | Anal. | ppm | H content |
| 1 | C | 73.74 | 73.70 | 0.9-2.5 | 14 | C | 69.21 | 69.18 | 0.9-2.5 | 14 |
| | H | 8.25 | 8.23 | 1.8-2.2 | 1(NH) | H | 7.74 | 7.74 | 6.5-8.5 | 1(NOH) |
| | N | 11.46 | 11.50 | 6.5-7.6 | 5 | N | 10.76 | 10.75 | 6.5-7.6 | 5 |
| | O | 6.55 | — | | | O | 12.29 | — | | |
| 2 | C | 66.86 | 66.90 | 1.3-2.5 | 9 | C | 63.71 | 63.70 | 1.3-2.5 | 9 |
| | H | 5.30 | 5.28 | 3.5-4.8 | 1(NH) | H | 5.05 | 5.03 | 8.0-10.0 | 1(NOH) |
| | N | 13.00 | 13.01 | 6.5-7.6 | 7 | N | 12.38 | 12.37 | 6.5-8.5 | 7 |
| | O | 14.84 | — | | | O | 18.86 | — | | |
| 3 | C | 68.55 | 68.52 | 0.8-3.0 | 20 | C | 66.04 | 66.03 | 0.8-3.0 | 20 |
| | H | 6.71 | 6.70 | 3.5-4.8 | 1(NH) | H | 6.47 | 6.45 | 8.0-10.0 | 1(NOH) |
| | N | 13.32 | 13.32 | 6.5-8.5 | 7 | N | 12.83 | 12.83 | 6.5-8.5 | 7 |
| | O | 11.42 | — | | | O | 14.66 | — | | |
| 4 | C | 77.52 | 77.55 | 0.9-2.5 | 14 | C | 73.52 | 73.51 | 0.9-2.5 | 14 |
| | H | 7.53 | 7.54 | 1.8-2.2 | 1(NH) | H | 7.14 | 7.14 | 6.5-8.5 | 1(NOH) |
| | N | 9.52 | 9.50 | 7.0-8.5 | 7 | N | 9.03 | 9.02 | 7.0-8.5 | 7 |
| | O | 5.43 | — | | | O | 10.31 | — | | |
| 5 | C | 73.19 | 73.18 | 1.2-2.5 | 16 | C | 69.43 | 69.43 | 1.2-2.5 | 16 |
| | H | 7.17 | 7.20 | 1.8-2.2 | 1(NH) | H | 6.80 | 6.77 | 6.5-8.5 | 1(NOH) |
| | N | 14.22 | 14.22 | 6.8-8.2 | 4 | N | 13.49 | 13.52 | 6.8-8.2 | 4 |
| | O | 5.42 | — | | | O | 10.28 | — | | |
| 6 | C | 77.52 | 77.50 | 0.8-2.5 | 14 | C | 73.52 | 73.49 | 0.8-2.5 | 14 |
| | H | 7.53 | 7.52 | 1.8-2.2 | 1(NH) | H | 7.14 | 7.16 | 6.5-8.5 | 1(NOH) |
| | N | 9.52 | 9.50 | 7.0-9.0 | 7 | N | 9.03 | 9.02 | 7.0-9.0 | 7 |
| | O | 5.43 | — | | | O | 10.31 | — | | |

TABLE 4-continued

Table 2$^{nd}$-1

| | | Compound C | | | | | Compound D | | | |
|---|---|---|---|---|---|---|---|---|---|---|
| | | Elemental Analysis | | $^1$H-NMR | | | Elemental Analysis | | $^1$H-NMR | |
| | | | | | H | | | | | H |
| Example | El. | Calcd. | Anal. | ppm | content | El. | Calcd. | Anal. | ppm | content |
| 7 | C | 66.04 | 66.01 | 1.0-4.5 | 8 | C | 61.53 | 61.52 | 1.0-4.5 | 8 |
| | H | 6.47 | 6.47 | 1.8-2.2 | 1(NH) | H | 6.02 | 6.02 | 6.5-8.5 | 1(NOH) |
| | N | 12.83 | 12.85 | 6.3-8.5 | 5 | N | 11.96 | 11.93 | 6.3-8.5 | 5 |
| | O | 14.66 | — | | | O | 20.49 | — | | |
| 8 | C | 61.51 | 61.50 | 1.0-4.5 | 8 | C | 57.58 | 57.56 | 1.0-4.5 | 8 |
| | H | 6.02 | 6.02 | 1.8-2.2 | 1(NH) | H | 5.64 | 5.62 | 6.5-8.5 | 1(NOH) |
| | N | 11.96 | 11.95 | 7.0-8.5 | 5 | N | 11.19 | 11.19 | 7.0-8.5 | 5 |
| | O | 6.83 | — | | | O | 12.78 | — | | |
| | S | 13.68 | 13.71 | | | S | 12.81 | 12.83 | | |
| 9 | C | 70.33 | 70.32 | 1.3-2.5 | 6 | C | 66.66 | 66.63 | 1.3-2.5 | 6 |
| | H | 4.86 | 4.88 | 3.5-4.8 | 1(NH) | H | 4.61 | 4.58 | 8.0-10.0 | 1(NOH) |
| | N | 19.30 | 19.29 | 5.8-8.5 | 7 | N | 18.29 | 18.32 | 5.8-8.5 | 7 |
| | O | 5.51 | — | | | O | 10.44 | — | | |
| 10 | C | 76.35 | 76.35 | 3.5-4.8 | 1(NH) | C | 73.68 | 73.65 | 8.0-10.0 | 1(NOH) |
| | H | 3.66 | 3.62 | 7.0-10.5 | 15 | H | 3.53 | 3.52 | 7.0-10.5 | 15 |
| | N | 12.72 | 12.75 | | | N | 12.27 | 12.29 | | |
| | O | 7.27 | — | | | O | 10.52 | — | | |

TABLE 5

Table 2$^{nd}$-2

| | | Compound C | | | | | Compound D | | | |
|---|---|---|---|---|---|---|---|---|---|---|
| | | Elemental Analysis | | $^1$H-NMR | | | Elemental Analysis | | $^1$H-NMR | |
| | | | | | H | | | | | H |
| Example | El. | Calcd. | Anal. | ppm | content | El. | Calcd. | Anal. | ppm | content |
| 11 | C | 68.27 | 68.26 | 1.0-3.8 | 12 | C | 64.10 | 64.10 | 1.0-2.5 | 12 |
| | H | 7.37 | 7.36 | 1.8-2.2 | 1(NH) | H | 6.92 | 6.90 | 6.5-8.5 | 1(NOH) |
| | N | 11.37 | 11.37 | 6.3-8.2 | 5 | N | 10.68 | 10.70 | 6.3-8.2 | 5 |
| | O | 12.99 | — | | | O | 18.30 | — | | |
| 12 | C | 47.13 | 47.15 | 1.0-2.5 | 6 | C | 45.45 | 45.44 | 1.0-2.5 | 6 |
| | H | 3.26 | 3.25 | 1.8-2.2 | 1(NH) | H | 3.14 | 3.12 | 8.0-10.0 | 1(NOH) |
| | N | 12.93 | 12.91 | 6.5-7.6 | 7 | N | 12.47 | 12.60 | 6.5-9.5 | 7 |
| | O | 18.46 | — | | | O | 21.37 | — | | |
| | Se | 18.22 | 18.23 | | | Se | 17.57 | 17.58 | | |
| 13 | C | 64.73 | 64.73 | 0.8-3.5 | 17 | C | 61.61 | 61.65 | 0.8-3.5 | 17 |
| | H | 6.71 | 6.70 | 1.8-2.2 | 1(NH) | H | 6.39 | 6.37 | 6.5-8.5 | 1(NOH) |
| | N | 13.32 | 13.30 | 7.0-8.5 | 3 | N | 12.68 | 12.62 | 7.0-8.5 | 3 |
| | O | 5.07 | — | | | O | 9.65 | — | | |
| | S | 10.17 | 10.20 | | | S | 9.67 | 9.71 | | |
| 14 | C | 70.80 | 70.80 | 0.8-4.5 | 19 | C | 67.08 | 67.06 | 0.8-4.5 | 19 |
| | H | 8.39 | 8.40 | 1.8-2.2 | 1(NH) | H | 7.95 | 7.92 | 6.5-8.5 | 1(NOH) |
| | N | 9.71 | 9.70 | 5.8-8.5 | 4 | N | 9.20 | 9.18 | 5.8-8.5 | 4 |
| | O | 11.10 | — | | | O | 15.77 | — | | |
| 15 | C | 73.10 | 73.09 | 0.8-3.5 | 8 | C | 69.14 | 69.12 | 0.8-3.5 | 8 |
| | H | 6.13 | 6.10 | 3.5-4.8 | 1(NH) | H | 5.80 | 5.78 | 8.0-10.0 | 1(NOH) |
| | N | 15.04 | 15.02 | 6.0-8.5 | 8 | N | 14.23 | 14.25 | 6.0-8.5 | 8 |
| | O | 5.73 | — | | | O | 10.83 | — | | |

Resolving the spirooxazine radical derivatives obtained by the above in chloroform and irradiating ultraviolet light or visible light resulted that two different absorption peaks were observed by ultraviolet-visible spectrophotometer. Decrease-increase change of the one side absorption peak was observed corresponding to increase-decrease change of the other side absorption peak. In addition, what observing the spectral absorption in the visible range of 400 nm to 800 nm could have been visually confirmed the reversible change of coloring and decoloring.

INDUSTRIAL APPLICABILITY

The spirooxazine radical derivatives of the present invention induce reversible change in light absorption spectrum with two different absorption peaks for each wavelength light, when they are resolved in organic solvents or polymers and are irradiated ultraviolet light or visible light. In particular, when they have spectrum absorption in visible range, they change reversibly between coloring and decoloring. These reversible changes induce oxidation-reduction potential changes and generate electron exchange depending on the state of chemical species in each wavelength light. Therefore, they are usable for various applications by using their properties.

The invention claimed is:

1. Spirooxazine-like radical compounds of the following formula (1):

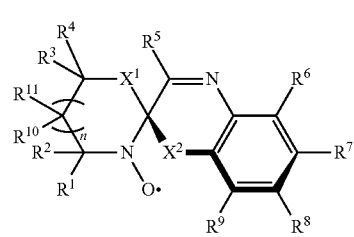

wherein, $X^1$ is a chalcogen element, alkylidene or cycloaklylidene group, $X^2$ is a sulfur atom, $R^1$ to $R^{11}$ are, independently each other, hydrogen atom, alkyl with 1 to 4 carbons, alkoxy, aryl, halogenated alkyl, cyano, amino, or nitro group, or halogen atom, or any of $R^1$ to $R^{11}$ bonded to carbon atoms adjacent to each other may form in combination an aromatic or heterocyclic ring; and n is 0 or 1.

2. The spirooxazine-like radical compounds according to claim 1, wherein n is 0, in the formula (1).

3. The spirooxazine-like radical compounds according to claim 1, wherein n is 1, in the formula (1).

4. A method for preparing a ring-opened body from the spiro type structure of the spirooxazine-like radical compound, or the spiro type structure from the ring-opened body of spirooxazine-like radical compound by reversible isomerization reaction between the spiro type structure in formula (1) and the ring-opened body in formula (2) of the spirooxazine-like radical compound, as shown in the following reaction scheme I, Reaction Scheme I

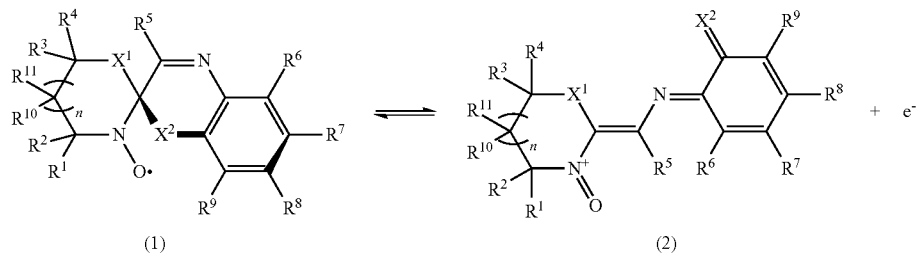

wherein, $X^1$, $X^2$, $R^1$ to $R^{11}$; and n are the same as described in claim 1.

5. The method according to claim 4, wherein n is 0, in the reaction scheme I.

6. The method according to claim 4, wherein n is 1, in the reaction scheme I.

* * * * *